(12) United States Patent  (10) Patent No.: US 6,517,512 B1
Bock et al.                  (45) Date of Patent:     Feb. 11, 2003

(54) HEART LUNG MACHINE SUCTION DEVICE WITH SENSOR

(75) Inventors: Herbert Bock, Nörten-Hardenberg (DE); Andreas Knorr, Göttingen (DE)

(73) Assignee: Cardiosmart SA, Fribourg (CH)

( * ) Notice: Subject to any disclaimer, the term of this patent is extended or adjusted under 35 U.S.C. 154(b) by 0 days.

(21) Appl. No.: 09/297,959

(22) PCT Filed: Nov. 3, 1997

(86) PCT No.: PCT/DE97/02540
§ 371 (c)(1),
(2), (4) Date: Jul. 16, 1999

(87) PCT Pub. No.: WO98/21094
PCT Pub. Date: May 22, 1998

(30) Foreign Application Priority Data

Nov. 11, 1996 (DE) .......................................... 196 46 410

(51) Int. Cl.[7] .............................................. A61M 31/00
(52) U.S. Cl. ................................... 604/67; 128/DIG. 3
(58) Field of Search ............................. 604/27, 28, 30, 604/31, 35, 540, 541, 65–67, 245, 246, 4.01; 128/DIG. 3; 250/574, 577; 623/3.1, 3.28; 600/342, 473, 476, 478, 573, 576, 578, 579

(56) References Cited

U.S. PATENT DOCUMENTS

| 3,799,702 | A | * | 3/1974 | Weishaar ...................... 417/38 |
| 4,082,959 | A |   | 4/1978 | Nakashima ................. 250/577 |
| 4,156,149 | A |   | 5/1979 | Vaccari ....................... 250/577 |
| 4,274,705 | A |   | 6/1981 | Miller ...................... 350/96.15 |
| 4,329,017 | A | * | 5/1982 | Kapany et al. .......... 350/96.15 |
| 4,396,353 | A | * | 8/1983 | MacDonald ................. 417/36 |
| 4,468,567 | A |   | 8/1984 | Sasano et al. .............. 250/577 |
| 4,994,682 | A |   | 2/1991 | Woodside .................... 250/577 |
| 5,005,005 | A |   | 4/1991 | Brossia et al. .............. 340/604 |
| 5,017,775 | A | * | 5/1991 | Granz et al. ........... 250/227.25 |
| 5,534,708 | A | * | 7/1996 | Ellinger et al. ............. 250/577 |

FOREIGN PATENT DOCUMENTS

WO    WO 87/07946    12/1987

* cited by examiner

Primary Examiner—Michael J. Hayes
(74) Attorney, Agent, or Firm—Seed IP Law Group PLLC

(57) ABSTRACT

Suction device, in particular for a heart and lung machine, comprising an aspirator, a suction line, and a suction pump, whereby the aspirator has a sensor to detect liquid, which sensor is connected to the suction pump via a signal line. The sensor is designed as an optical element in which light can be passed on by total reflection depending upon the surrounding medium.

14 Claims, 5 Drawing Sheets

HEART LUNG MACHINE SUCTION DEVICE WITH SENSOR

BACKGROUND OF THE INVENTION

Technical Field

Figure 1:
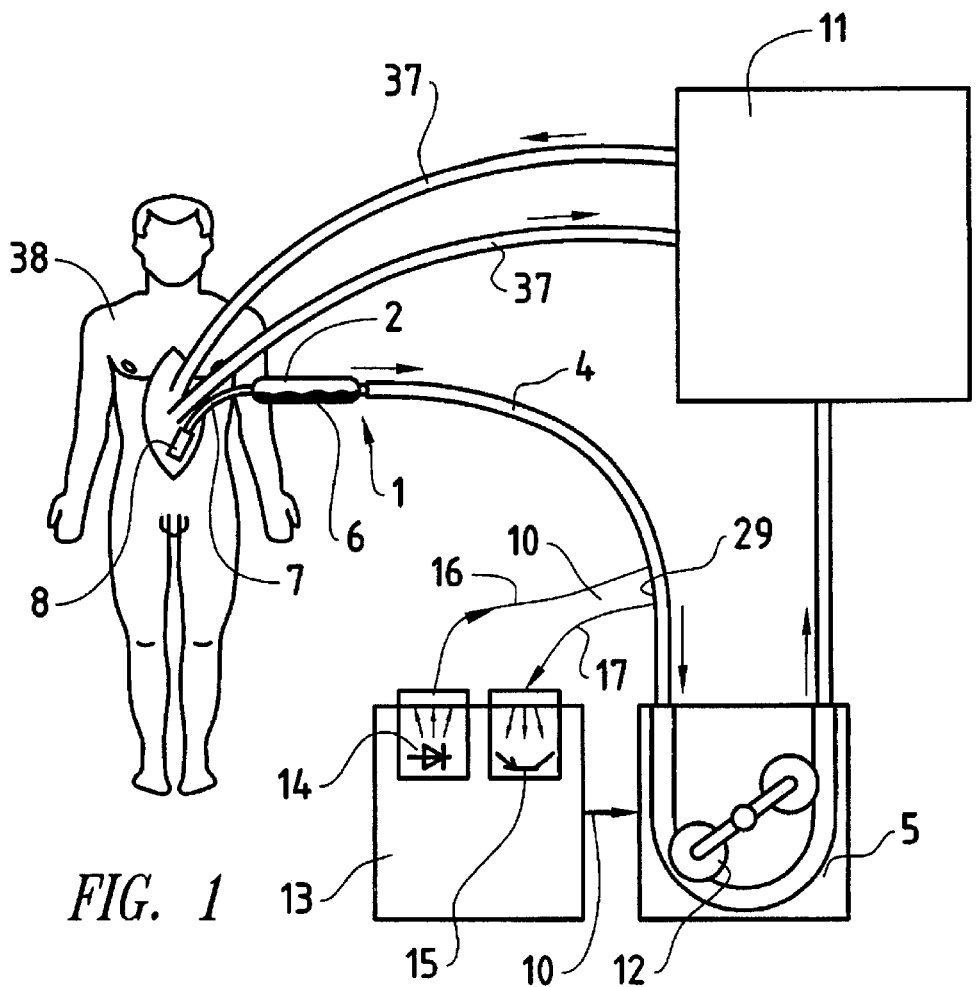

The invention relates to a suction device, in particular for a heart-lung machine, comprising an aspirator, a suction line and a suction pump.

The invention relates furthermore to a method for switching on and off a pump which is used in particular in combination with a heart-lung machine and which suctions up a liquid through an aspirator.

In order to work on and in the heart during heart operations, with the aid of heart-lung machine, the blood of the patient is diverted into the heart-lung machine through tubes, which are inserted into the large veins of the body, and after saturation of the blood with oxygen in an oxygenator, and is led back to the patient with a hose pump or a centrifugal pump through a cannula which opens out into the aorta. By clamping off, or respectively pinching, the large blood vessels close to the heart, the heart is taken out of the blood circulation. The necessary operative procedure can be carried out on a bloodless heart. Although the main portion of the blood runs through the heart-lung machine, blood oozes out of the surgical wounds into the heart and lung cavity as well as out of the pulmonary vascular bed into the heart. In the case of congenital heart defects, up to 40% of the circulating blood can inundate the heart and thus the operation region, so that the surgeon loses sight of the defect to be corrected in and on the heart. During use of the heart-lung machine in an average heart operation of about 90 to 120 minutes, up to 40 liters of blood can accumulate. This blood cannot be returned directly to the circulation, but instead is suctioned up separately through a suction device associated with the heart-lung machine, and after deaeration and microfiltration, is fed back to the circulation in a continuous way. In the case of careful work without any complications, blood loss during heart operations is very minimal. A high percentage of patients need no foreign blood up until their release from the hospital.

In the known suction devices suitable for heart surgery, an aspirator, on whose free end an aspirator tip with suction openings has been disposed, is connected to a suction pump via a suction line. The suction line is designed as a PVS or silicon hose, which can be inserted into a U-shaped pump body of the suction pump constructed as a hose pump. Two opposite rollers are led over the hose at up to 250 revolutions per minute, and thereby suction up the accumulating blood out of the operation region through the aspirator, with its suction tip placed in the operation region, and lead the blood into a blood reservoir (cardiotomy reservoir). During the suction procedure a quantity of air is suctioned up as well. The suctioned up blood-air mixture presents a special problem since damage to the blood corpuscles and to the coagulation system of the blood occur through the arising shear forces and through the direct air contact. Gentle treatment with the aspirators and avoidance of air admixture is an important prerequisite for the well-being of the patient after the operative procedure. Owing to the disposition of the heart-lung machine with respect to the patient, the operator of the machine (cardiotechnician) has no view into the operation region and no eye contact with is the surgeon. Disadvantageous therefore is that the switching on and off or respectively the control of the suction pump must take place on the basis of a shout from the surgeon or respectively on the basis of the suction sound. This situation, above all in critical situations, results in situations of stress for surgeons and cardiotechnicians.

SUMMARY OF THE INVENTION

Object of the present invention is therefore to improve a suction device, which is especially suitable for a heart-lung machine, in such a way that the suction pump switches on and off automatically.

The object is achieved according to the invention in that the aspirator has a sensor to detect fluid, which sensor is connected to the suction pump via a signal line.

Through the placement of the sensor in the aspirator it is possible to distinguish liquid from air and to start the suction pump when liquid is present, i.e. when blood is present, and to stop the suction pump automatically upon admission of air. Vortices of air with the blood are thereby minimized, and the suctioning up of blood no longer has to be started by the surgeon by shouting.

According to a preferred embodiment of the invention, the sensor is disposed in the region of a free end, remote from the suction pump, of a suction tip of the aspirator. By disposing the sensor in the region of the aspirator tip, the fluid to be suctioned up can be detected early in the vicinity of the suction openings disposed on the tip.

According to a further preferred embodiment, the sensor is designed as an optical element in which, depending upon the surrounding medium, light can be passed on by total reflection. A sensor unit has a laser diode as the optical transmitter, which is connected to the optical element via a first light guide. The sensor unit has furthermore an optical receiver, which is designed as a photodiode and is connectible to the sensor via a second light guide as part of the signal line. If the optical element is surrounded by liquid, or respectively blood, the light reflected by the laser diode via the first light guide into the optical element will be at least partially decoupled in the liquid. If the optical element is surrounded by air, the light of the laser diode coupled in the optical element is passed on through total reflection in the optical element, and reaches the optical receiver, designed as a photodiode, via the second light guide. By using an optical transmitter in connection with light guides, it is possible to forego an electrically conducting connection between sensor and sensor unit, which is of particular safety-technical significance during use on a patient. By means of this configuration moreover not only a qualitative but also a quantitative control of the suction pump is possible.

According to a further preferred embodiment, the optical element is designed as a light guide fiber piece with the cladding surface as the optical interface. It is thereby possible for first light guide, optical element and second light guide to be formed by a continuous light guide fiber.

According to a further preferred embodiment of the invention, optical transmitter and optical receiver are connected to the optical element through the same optical light guide. Transmitter and receiver are thereby connected via a Y coupler with the front face of the light guide turned toward them. This has the advantage that it is possible to use just one light guide fiber as the light guide, saving space. Moreover it is possible to form the optical element—for example as a tip of a cone—on the light guide's front face remote from the sensor unit.

Disadvantageous in the known methods for switching a suction pump on and off, used especially in combination with a heart-lung machine, is that the suction pump connected to the aspirator has to be switched on and off by hand.

A further object of the invention, therefore, is to improve a method for switching a suction pump on and off, which is used in particular in combination with a heart-lung machine, in such a way that an automatic switching on and off of the pump is possible.

This object is achieved in that a sensor disposed on the aspirator detects fluid to be suctioned up, and emits a sensor signal for automatic switching on and off of the pump.

Through the detection of the fluid to be suctioned up and through the emission of a sensor signal, an automatic suctioning up, or respectively a automatic switching on and off of the suction pump, is made possible. The suctioning up no longer has to be started by a shout. Through the detection of the fluid, the traumatization of the blood through air impurities is reduced during the suctioning up of blood.

According to a preferred embodiment of the method, a sensor signal is received from sensor electronics of a sensor unit, is evaluated, and is passed on to the suction pump as the control signal. This allows not only a qualitative, but also a quantitative control of the suction device.

According to a further preferred embodiment of the method, a light signal is supplied to the sensor from an optical transmitter, which signal the sensor passes on in air to an optical receiver, and in liquid diverts at least partially into the liquid. The light signal is passed on thereby in a light guide fiber from the optical transmitter to the sensor and from the sensor to the optical receiver by total reflection.

By using an optical sensor with optical signal line, an electrical connection between aspirator and sensor unit can be omitted.

Further particulars of the invention result from the following detailed description and the enclosed drawings, in which preferred embodiments of the invention are illustrated by way of example.

BRIEF DESCRIPTION IF THE DRAWINGS

Figure 2:
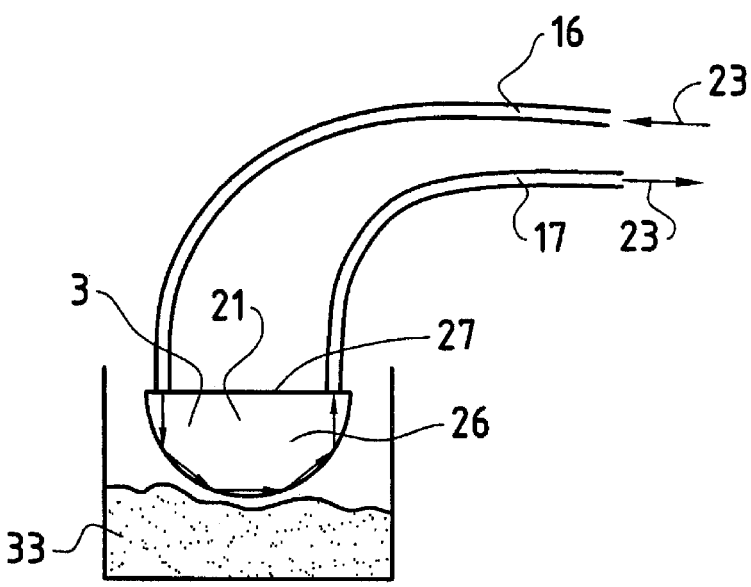
Figure 3:
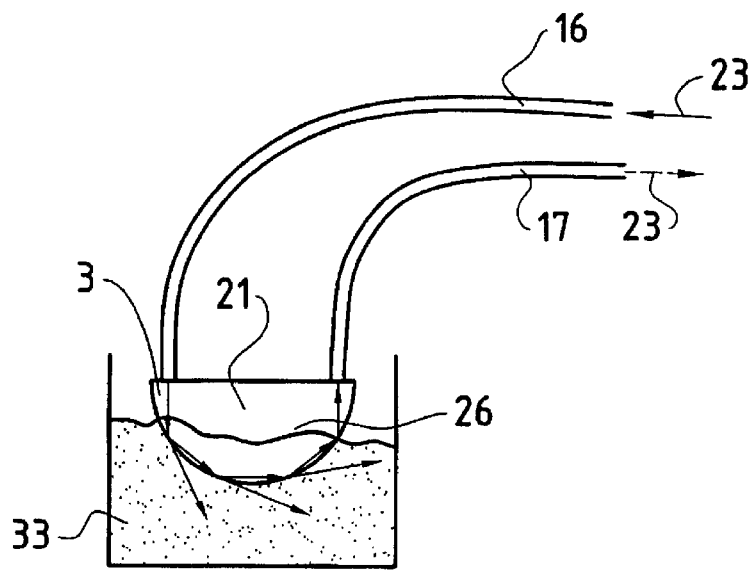
Figure 4:
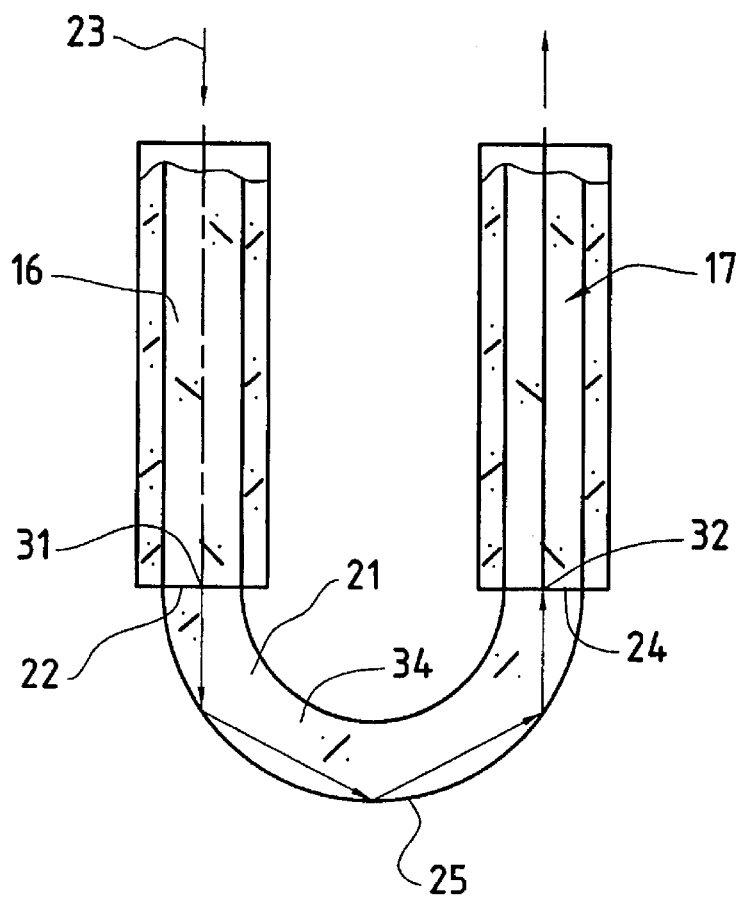
Figure 5:
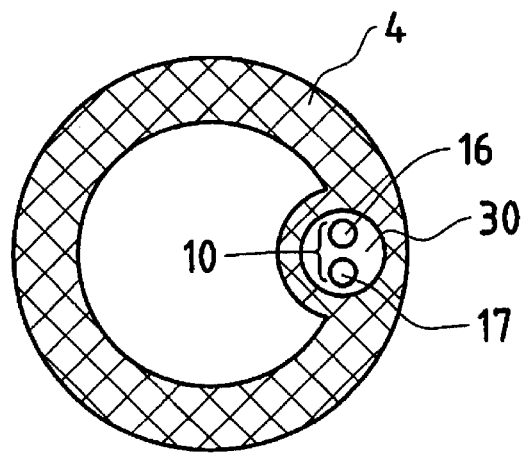
Figure 6:
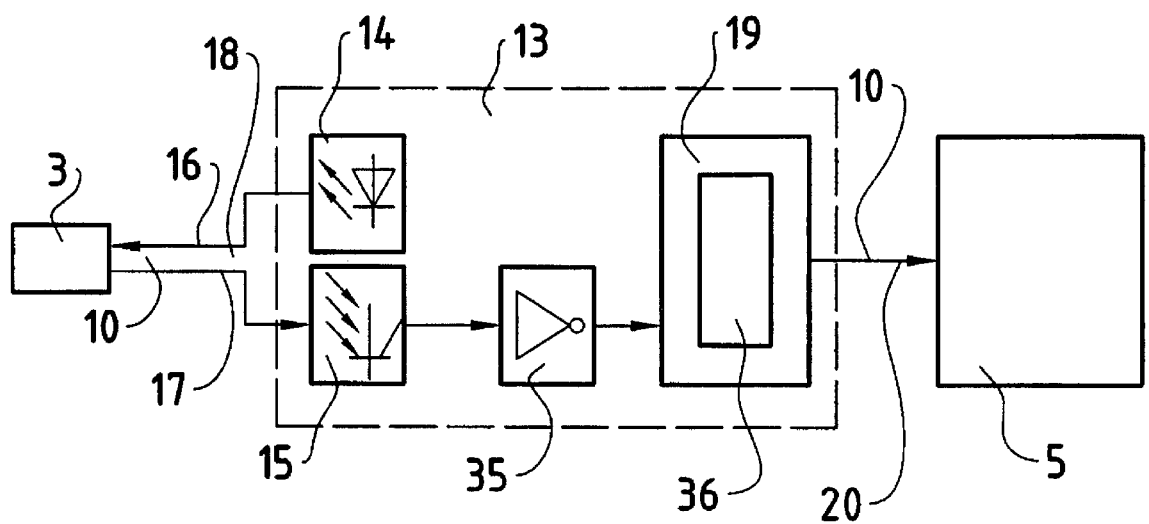
Figure 7:
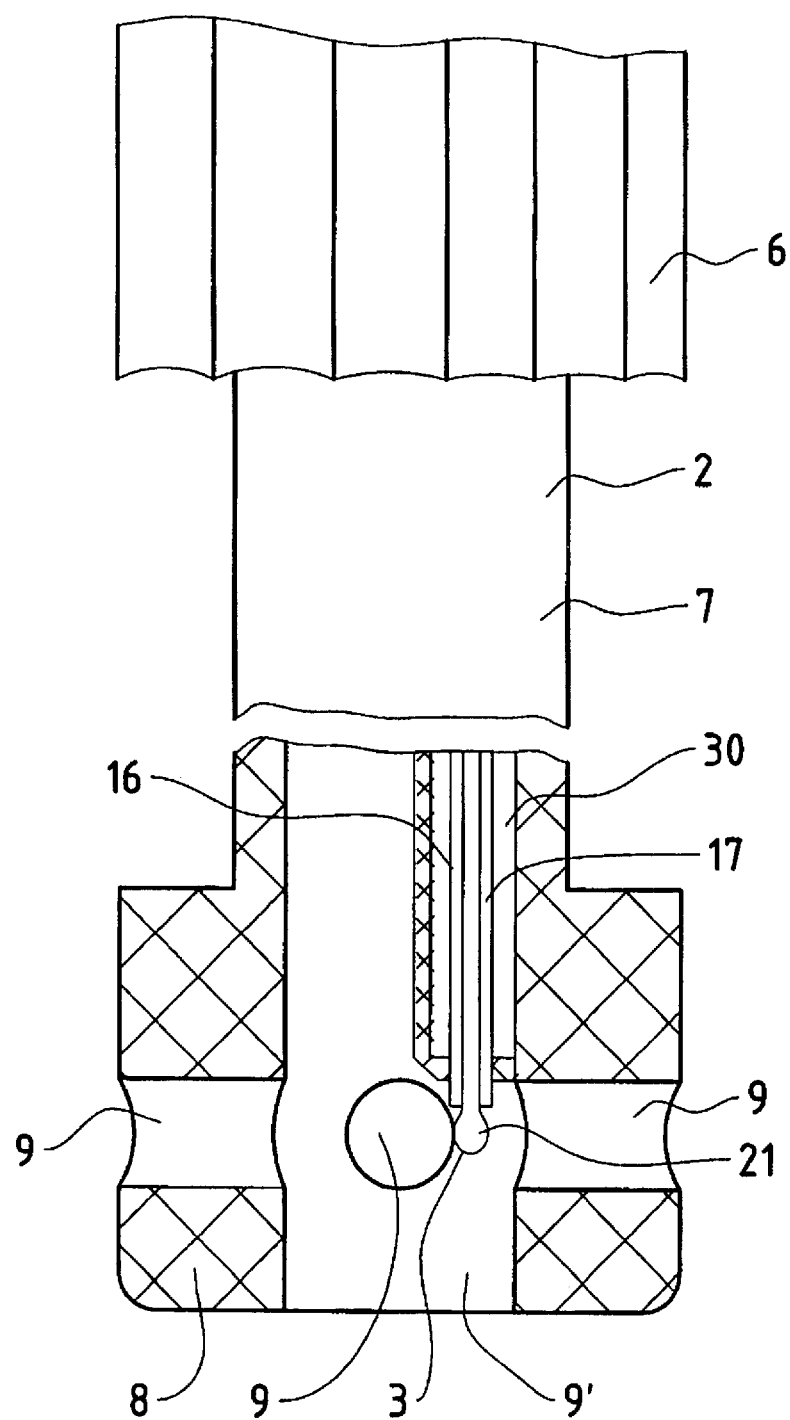
Figure 8:
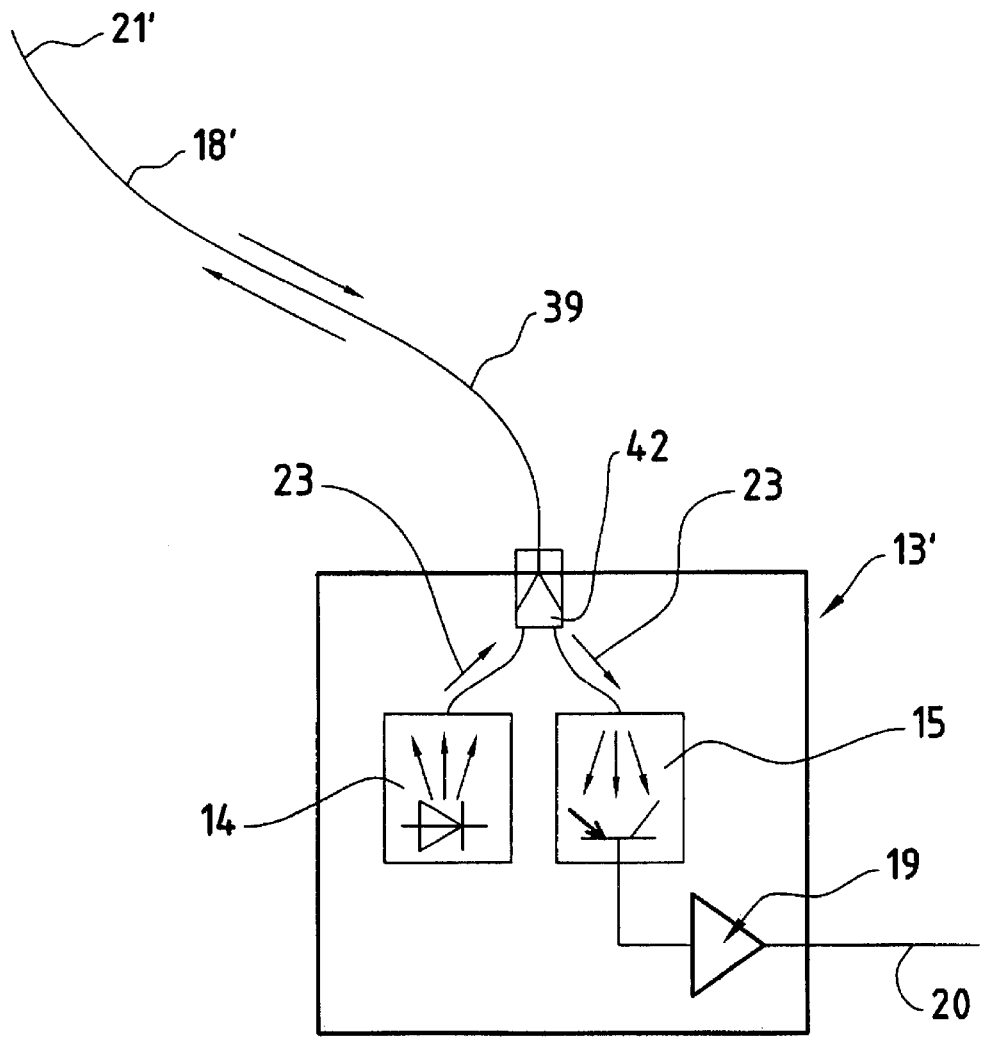

Shown in the drawings are:

FIG. 1: a schematic representation of a suction device in connection with a heart-lung machine, FIG. 2: an enlarged schematic representation of a sensor surrounded by air, FIG. 3: an enlarged schematic representation of the sensor of FIG. 2 surrounded by liquid, FIG. 4: an enlarged schematic representation of a sensor surrounded by air, FIG. 5: a cross-section through a suction line with light guides situated on the inside;

FIG. 6: a schematic representation of the signal flow of a suction device;

FIG. 7: a side view of an aspirator, depicted enlarged, partially in section;

FIG. 8: a schematic representation of a light guide with a sensor unit, and

Figure 9:
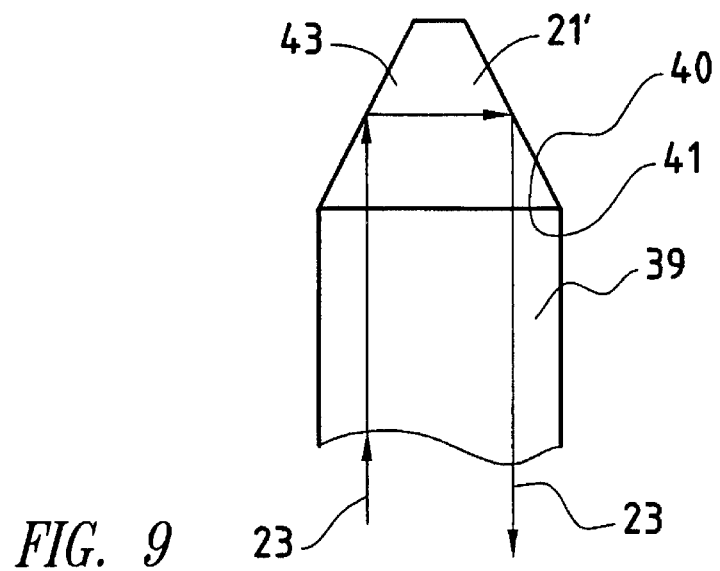

FIG. 9: an enlarged, schematic representation of a sensor, surrounded by air, on a light guide.

DETAILED DESCRIPTION OF THE INVENTION

A suction device (1) comprises essentially an aspirator (2) with a sensor (3), a suction line (4) and a suction pump (5).

The aspirator (2) has a handle part (6), which is connected to an aspirator tip (8) via an interim piece (7). Disposed on the aspirator tip (8) is a plurality of suction openings (9). In principle it is also possible, however, to have just one suction opening (9'). On the interior of the aspirator tip (8) a sensor is disposed adjacent to a suction opening. The sensor is connected to the suction pump (5) via a signal line (10). The aspirator (2) is connected on its handle part's (6) end remote from the aspirator tip (8) to the suction line (4), which is connected to the heart-lung machine (11) via the suction pump (5). The suction line (4) is designed as a PVC or silicon hose with usual interior diameter of 6, 8 or 10 mm. The suction pump (5) is designed as a double roller hose pump. A vacuum pump or another suitable pump can also be used, however. The double roller hose pump has a U-shaped pump body (12), in which the suction line (4) is inserted. A sensor unit (13) is disposed in front of the suction pump (5). The sensor unit (13) is connected via a signal line (10), on the one side to the sensor (3) and on the other side to the suction pump (4) <sic. (5)>. The sensor unit (13) has an optical transmitter (14) and an optical receiver (15). The optical transmitter (14), designed as a laser diode, is connected to the sensor (3) via a first light guide (16). The sensor (3) is connected to the optical receiver (15) via a second light guide (17). The optical receiver (15) is designed as a phototransistor or as a photodiode. The signal line (10) between the sensor (3) and the sensor unit (13) is thus designed as an optical signal line (18) consisting of first light guide (16) and second light guide (17). The sensor unit (13) amplifies and negates, or respectively inverts, the sensor signal of the sensor (3) arriving at its optical receiver (15) with a negator (35), evaluates the sensor signal with sensor electronics (19) according to a programmable procedure by means of a microprocessor (36), and emits an electrical control signal to the suction pump (5) via the control line (20).

The sensor (3) is designed as an optical element (21) in which, depending upon the surrounding medium, light (23) reflected in via an input face (22) is passed on to an output face (24) by total reflection. The refraction index of the optical element (21) is selected in such a way that with air as the surrounding medium the light is passed on in the interior by total reflection, and with liquid, or respectively blood, as the surrounding medium, the light (23) is diverted into the liquid via the cladding surface, or respectively interface (25).

The optical element (21) has the shape of a spherical segment, or respectively a hemisphere (26), in which the input face (22) and the output face (24) are disposed on the cut face (27). It is also possible, however, to design the optical element (21) as approximately half a multi-faced polyhedron.

According to another embodiment, the optical element (21) is designed as an approximately semicircular or U-shaped, curved light guide element (28). A light guide fiber also comes into consideration as optical element (21), however, which uses its cladding surface in the sensor region as the interface for the total reflection (25). The signal line (10), or respectively the optical signal line (18), is led, in a channel (30) disposed in the suction line (4), up to a branch point (29) situated in front of the suction pump (5). The first light guide (16) has a light output face (31) on its end remote from the optical transmitter (14), on which light output face the first light guide (16) is connected to the input face (22) of the optical element (21). The second light guide (17) has on its end remote from the optical receiver (15) a light input face (32), via which the second light guide is connected to the output face (24) of the optical element (21). The optical transmitter (14) shines light (23) via the end of the first light guide (16) turned towards it into the first light guide (16), a synthetic or glass fiber. The light (23) is reflected via the light output face (31) of the first light guide (16) into the optical element (21) via its input face (22). If air surrounds the optical element (21), the light shone into the optical element (21) is led by means of total reflection to its output face (24) and further via the light input face (32) of the second light guide (17) to the optical receiver (15).

According to another preferred embodiment of the invention, optical transmitter (14) and optical receiver (15) are connected to the optical element (21') via the same optical light guide (39). Transmitter (14) and receiver (15) are thereby connected via a Y coupler (42) or another optical element to the front face of the light guide (39) turned toward them. The optical element (21') has a coupling surface (40) which is adjacent to a front face (41) of the light guide (39) turned away from the sensor unit (13'). The optical element is thereby constructed in such a way that light (23) coming in on its coupling surface (40) turned toward the light guide (39), with air as the surrounding medium, is totally reflected on its interface (25') spanning the coupling surface (40), and is led back again via the coupling surface (40), the light (23) being sent on to the optical receiver (15) via the Y coupler (42). If the optical element (21') is surrounded by liquid (33) at its interface (25'), the light (23) will be diverted at least partially into the liquid via the interface (25'). This has the advantage that only one light guide fiber needs to be used as the light guide (39), saving space for the optical signal line (18'). Moreover it is possible to build the optical element (21')—for example as a tip of a cone or respectively as a frustum (43)—on the light guide's (39) front face (41) remote from the sensor unit (13'). It is also possible, however, to construct the optical element (21') as a kind of prism with at least two interfaces (25") running toward each other at an angle or respectively to the light guide (39).

The light guide (16, 17, 39) is designed as a light guide fiber. The light guide fiber is made of synthetic material. Use of light guide fibers made of glass is also possible, however. The light guide (16, 17, 39) can also be formed from a plurality of light guide fibers.

The signal of the optical receiver (15) is supplied to the negator (35), which amplifies the signal, and sends it in negated, or respectively inverted, form to the sensor electronics (19), which evaluate the signal and pass it on as a switch-off signal to the suction pump (5) via the control line (20). With liquid, or respectively blood, as the medium surrounding the optical element (21), the light (23) reflected via the input face (22) of the optical element (21) into the optical element is radiated into the liquid, or respectively blood. No light or respectively only greatly diminished light (23) thereby reaches the optical receiver (15), so that the sensor unit (13) gives a switch-on signal to the suction pump (5) via the control line (20), whereby the suction process is set in motion. Upon receiving values lying between the extreme values, the suction process is correspondingly decreased or respectively accelerated.

The blood suctioned up by the suction device (1) is fed to the heart-lung machine (11) through the suction line (4), which machine is connected to the blood circulation of a patient (38) through tubes (37).

The suction device (1) according to the invention is especially suited for use with a heart-lung machine (11). It is also possible, however, to use the suction device (1) in a very general way for suctioning up liquids. The sensor designed as an optical element (21) can also be used in a very general way for detecting fluids or respectively as a level sensor.

What is claimed is:

1. A medical device, comprising:
    a heart-lung machine;
    an aspirator;
    a suction line and a suction pump coupled between the aspirator and the heart-lung machine; and
    a sensor in the form of an optical element, which has an effect upon the suction pump via an optical signal line and a sensor unit, connected in series, having an optical transmitter and an optical receiver and connected to the suction pump, wherein the optical transmitter and the optical receiver are connected to the optical element via a same optical light guide as the optical signal line, where with air as a surrounding medium the optical element totally reflects light coming in on a coupling surface adjacent to a front face of the optical light guide on its interface spanning the coupling surface, and guides the light back via the coupling surface, and with liquid as the surrounding medium diverts the light at least partially via an interface into the liquid wherein a transmitter and a receiver are connected to a front face of the light guide via a Y coupler.

2. A medical device, comprising:
    a heart-lung machine;
    an aspirator;
    a suction pump coupled to the aspirator with a suction line and coupled to the heart-lung machine; and
    a sensor unit coupled to the suction pump with a signal line to control operation of the pump, the sensor unit including an optical transmitter and an optical receiver coupled to an optical element with a single wave guide, the optical element having a coupling surface adjacent a corresponding face of the wave guide, the optical element further having an interface surface that totally internally reflects light received from the optical transmitter when the interface surface is in contact with a gas and transmits through the interface surface at least a portion of light received from the optical transmitter when the interface surface is in contact with a liquid wherein the corresponding face of the wave guide is a first face, the wave guide having a second face spaced apart from the first face, the optical transmitter and the optical receiver being coupled to the second face of the wave guide with a Y-shaped coupler.

3. The device of claim 2 wherein the aspirator includes a free end having a tip spaced apart from the pump and the optical element is disposed in the tip.

4. The device of claim 2 wherein the sensor unit includes at least one electronic circuit coupled to the pump for converting a signal received from the sensor unit to a control signal for controlling the pump.

5. The device of claim 2 wherein the optical transmitter and the optical receiver include semiconductor elements.

6. The device of claim 2 wherein the optical transmitter includes a laser diode.

7. The device of claim 2 wherein the optical receiver includes a phototransistor.

8. The device of claim 2 wherein the interface surface of the optical element is at least partially defined by a portion of a multi-faced polyhedron.

9. The device of claim 2 wherein the interface surface of the optical element is at least partially defined by a frustum of a cone.

10. The device of claim 2 wherein at least a portion of the signal line extends though the suction line.

11. The device of claim 2 wherein the sensor unit includes a programmable microprocessor.

12. The device of claim 2 wherein the sensor unit includes at least one amplification circuit for amplifying a signal received from the optical element.

13. The device of claim 2 wherein the signal line includes an electrical line.

14. The device of claim 2 wherein the sensor unit is integrated with the suction pump.

* * * * *